(12) United States Patent
Chorev et al.

(10) Patent No.: US 7,799,757 B2
(45) Date of Patent: Sep. 21, 2010

(54) ANALOGS OF PARATHYROID HORMONE AND PTH-RELATED PROTEIN AS BONE ANABOLIC AGENTS

(76) Inventors: Michael Chorev, 203 South St., Chestnut Hill, MA (US) 02467; Michael Rosenblatt, 130 Lake Ave., Newton Centre, MA (US) 02159

( * ) Notice: Subject to any disclaimer, the term of this patent is extended or adjusted under 35 U.S.C. 154(b) by 466 days.

(21) Appl. No.: 10/516,224

(22) PCT Filed: Jun. 13, 2003

(86) PCT No.: PCT/US03/18890

§ 371 (c)(1), (2), (4) Date: Jun. 20, 2005

(87) PCT Pub. No.: WO03/105772

PCT Pub. Date: Dec. 24, 2003

(65) Prior Publication Data

US 2006/0058230 A1 Mar. 16, 2006

Related U.S. Application Data

(60) Provisional application No. 60/388,918, filed on Jun. 13, 2002, provisional application No. 60/398,005, filed on Jul. 23, 2002.

(51) Int. Cl.
*A61K 38/00* (2006.01)
*A61K 38/16* (2006.01)
*A61K 38/29* (2006.01)
*C07K 14/00* (2006.01)
*C07K 14/575* (2006.01)
*C07K 14/635* (2006.01)

(52) U.S. Cl. .............................. 514/12; 514/2; 530/300; 530/324; 530/399

(58) Field of Classification Search ....................... None
See application file for complete search history.

(56) References Cited

U.S. PATENT DOCUMENTS

| 5,747,456 A | 5/1998 | Chorev et al. | |
|---|---|---|---|
| 5,837,218 A * | 11/1998 | Peers et al. | 424/1.69 |
| 6,316,410 B1 | 11/2001 | Barbier et al. | |
| 6,537,965 B1 | 3/2003 | Bringhurst et al. | |
| 6,544,949 B1 * | 4/2003 | Dong | 514/12 |

FOREIGN PATENT DOCUMENTS

WO  WO 01/81415 A1 * 11/2001

OTHER PUBLICATIONS

Rudinger J, Characteristics of Amino acids as components of a peptide hormone sequence, Peptide Hormones, Edited by J.A. Parsons, Univerty Park Press, Jun. 1976.*
Sigma Genosys from http://www.sigma-genosys.com/peptide_design.asp, accessed Dec. 16, 2004.*
Berendsen HJC, A Glimpse of the Holy Grail?, Science, Oct. 23, 1998, 282: 642-643.*
Voet Donald and Voet Judith G, Biochemistry, Second Edition, John Wiley & Sons, Inc., 1995, 235-241.*

* cited by examiner

*Primary Examiner*—Julie Ha
(74) *Attorney, Agent, or Firm*—Wolf, Greenfield & Sacks, P.C.

(57) ABSTRACT

Novel parathyroid hormone analogs and parathyroid hormones-related protein analogs are described. Further, methods of using these analogs to treat osteoporosis, promote the formation of bone, and inhibit bone loss are described.

10 Claims, No Drawings

ANALOGS OF PARATHYROID HORMONE AND PTH-RELATED PROTEIN AS BONE ANABOLIC AGENTS

RELATED APPLICATIONS

This application is a national stage filing under 35 U.S.C. §371 of PCT International application PCT/US03/18890, filed Jun. 13, 2003, which was published under PCT Article 21(2) in English, and which claims the benefit under 35 U.S.C. §119(e) of U.S. provisional application 60/388,918, filed Jun. 13, 2002, and U.S. provisional application 60/398,005, filed Jul. 23, 2002, each of which is incorporated herein by reference.

GOVERNMENT SUPPORT

This work was funded in part by Grant Number DK47940 from the National Institutes of Health. Accordingly, the Government may have certain rights to this invention.

FIELD OF THE INVENTION

The invention relates to parathyroid hormone analogs and parathyroid hormone-related protein analogs and their use as bone anabolic agents. These analogs are useful for treating osteoporosis, promoting the formation of bone, and inhibiting bone loss.

BACKGROUND OF THE INVENTION

Osteoporosis is the most common form of metabolic bone disease. The term encompasses any disease or idiopathic cause that results in a reduction in the mass of bone per unit volume. Osteoporosis results in differing degrees of skeletal fragility sufficient to increase the risk of fracture. Typically, the resorption in bone mass results from an imbalance in the processes that influence the acquisition and maintenance of skeletal mass. Osteoporosis is the most common disorder in which all of the skeleton is. involved, and is an important cause of morbidity in the elderly. Post-menopausal women are at a particularly high risk for idiopathic osteoporosis.

In general, cancellous bone has higher turnover rate than cortical bone. In early years of menopause the rate of bone loss is substantially faster for vertebral cancellous bone than for cancellous bone at other sites and cortical bone. Usually, peak adult bone mass is reached between the ages of 30 and 35 for cortical bone and often even earlier for trabecular bone. After peak adult bone mass is reached, the rates of bone formation and resorption are typically approximately equal, and relatively low compared with the period of growth spurt. Normally, skeletal mass is maintained by the normal balance between bone formation and bone resorption.

Bone remodeling, including bone formation and resorption, is a continuous process. In healthy subjects, these complementary mechanisms maintain a steady bone mass per unit volume (referred to herein as "bone mass"). However, subjects that may have failed to obtain optimal skeletal mass during the first 30 years of life, and/or subjects wherein the rate of bone resorption exceeded the rate of bone formation after peak skeletal mass was obtained may develop osteoporosis.

Bone resorption typically precedes formation, but does not last as long as formation. As a result, there are typically more sites of active formation than of resorption. Unless formation compensates for resorption, the bone mass will decrease. After an age ranging from 40 to 50, cortical bone is lost at a rate of about 0.3 to 0.5% per year in both men and women. There is an accelerated loss of cortical bone superimposed on the age-related loss around the menopause in women. The cumulative losses of bone mass range from 20 to 30% in men and up to 50% in women. Remodeling activity is typically increased in women with post-menopausal osteoporosis, when compared with age-matched controls. The difference is even more striking when the bone remodeling activities of post-menopausal women are compared to pre-menopausal women. When the difference between the rates of bone formation and bone resorption is maintained, the loss of bone density may become so marked that the bone can no longer withstand normal mechanical forces to which it is subjected, resulting in bone fracture. Often, osteoporosis is only recognized as a clinical problem after a fracture has occurred.

In some instances, another disease, for example, Cushing's Syndrome or osteogenesis imperfecta, results in osteoporosis. In most cases, however, patients with osteoporosis do not appear to have any other disease. Osteoporosis, which occurs in children, young adults, and adults of both sexes with normal gonadal function, is referred to as idiopathic osteoporosis, although often the osteoporosis is of unknown pathogenesis.

There are agents available for preventing bone loss and treating established osteoporosis. The ability to measure bone density and predict bone fracture risk has changed the approach to treatment, as a clinical benefit of treatment can be measured in terms of improved bone mass as well as a decreased incidence of fractures. Most of the drugs that are available are inhibitors of bone resorption, although some agents, such as sodium fluoride, increase bone formation. Fluoride treatment suffers from a narrow therapeutic window and a lack of demonstration of reduction in fracture rate, probably due to the poor mechanical qualities of newly formed bone. The agents that are currently available and/or under investigation to treat osteoporosis include, but are not limited to, Selective Estrogen-Receptor Modulators (SERMs), estrogens, androgens, cathepsin K inhibitors, calcium supplements, vitamin D (and metabolites and analogs thereof, thiazide diuretics,-calcitonin (and analogs thereof), bisphosphonates, fluoride, integrin antagonists, parathyroid hormone, calcilytics, calcimimetics, inhibitors of Src tyrosine kinase and Src SH2 inhibitors.

However, the available agents to treat osteoporosis that are available to date suffer from several drawbacks. First, most available agents may inhibit bone resorption but do not promote bone formation. Additionally, many women are reluctant to use estrogens to prevent bone loss and/or treat osteoporosis because of the return of menstrual bleeding and the fear of an increased risk for endometrial and breast cancer. Testosterone has been shown to be useful to treat osteoporotic men with gonadal deficiency, but there has been no evidence of efficacy in men with no normal gonadal function. Some patients cannot tolerate the agents used to treat osteoporosis because of undesirable side-effects, such as knee, foot and ankle pain, and nausea. Additionally, none of the agents used to treat osteoporosis completely inhibit resorbtion and/or actively promote bone formation.

As a result, several groups have been investigating various types of agents to treat osteoporosis, alone, and in combination. Parathyroid hormone (PTH), parathyroid related-protein (PTHrP), and analogs thereof are among the many agents that have been proposed for the treatment of osteoporosis.

The normal function of PTH is to maintain extracellular fluid calcium concentration. PTH acts directly on bone and kidney and indirectly on the intestines. PTH production in healthy individuals is closely regulated by the concentration of serum ionized calcium. Tendencies towards hypocalcemia, for example, induced by a calcium-deficient diet, are balanced by an increased PTH secretion. The increase in PTH levels increases the rate of bone resorption, thereby increasing the calcium flow from bone into blood, reduces the renal clearance of calcium. and increases the efficiency of calcium absorption in the intestines.

The physiological role of the parathyroid hormone-related protein (PTHrP) is not fully understood, but is thought to be acting principally as a paracrine or autocrine factor. PTHrP plays a role in fetal development as well as in adult physiology. PTHrP is produced by many cell types, including brain, pancreas, heart, lung, memory tissue, placenta, endothelial, and smooth muscle cells. In adults, PTHrP is thought to have little to do with calcium homeostasis, except in disease states.

PTH and PTHrP are distinct proteins and products of different genes. However, they share a similar bioactivity profile and a very limited sequence homology, indicating that they may have evolved from a common ancestral gene. Eight out of the 13 first amino acid residues at the N-terminus are identical. Both PTH, an 84 amino acid residues peptide, and PTHrP, a 139 to 173 amino acid residues peptide, bind to the PTH receptor (often referred to as the PTH/PTHrP receptor) and stimulate the same intracellular signaling pathways.

The mature circulating form of parathyroid hormone is comprised of 84 amino acid residues. For most bone-related activities the truncated form of PTH, PTH(1-34), is a full agonist like the native 84 amino-acid hormone. Amino-terminal truncation results in polypeptides that are competitive antagonists of PTH-stimulated adenylate cyclase. For example, [Tyr$^{34}$]bPTH(7-34)NH$_2$ retains moderate affinity for renal PTH receptors, but does not have any agonist activity; weak receptor binding activity is retained in a fragment as small as PTH(25-34) (M. Rosenblatt, et al., *Endocrinol.*, (1980)107, 545-550). In contrast, carboxyl-terminal truncations of PTH(1-34) produce agonists with progressively lower affinities. PTH(1 -25) is reported to be essentially inactive (Segre, G. V., et. al., *J. Biol. Chem.* (1979) 254, 6980-6996; Rosenblatt, M., *Endocrinology of Calcium Metabolism*; Parsons, J. A., ed. (1982) Ravens Press, N.Y., 103-142; Tregear, et al., *Endocrinol.* (1973) 93, 1349-1353). The principal receptor-binding domain of PTH is reported to include amino acid residues 25-34 and the principal activation domain is reported to include amino acid residues 1-6.

Under some circumstances, PTH is a bone anabolic agent, and promotes bone formation. However, PTH can stimulate bone resorption as well. It has been reported that high-dose, continuous administration of PTH results in a lowered bone mass but low-dose, intermittent administration of PTH can increase bone mass. PTH administered continuously reportedly causes an increase in the number of bone cells, including osteoclasts, and an increase in bone remodeling. These increases reportedly are apparent within hours after PTH administration and persist for hours after PTH is withdrawn. PTH administration intermittently over days in humans and animals reportedly leads to a net stimulation of bone formation. For example, see Neer et al., *N. Engl. J Med.* 344:1434-1441, (2001). In contrast, continuous exposure to elevated levels of PTH leads to osteoclast-mediated bone resorption. Several groups have investigated the use of PTH and PTHrP analogs as agents to treat osteoporosis. These efforts are described in U.S. Pat. Nos. 5,747,456; 5,849,695; 4,656,250; 6,051,686; and 6,316,410.

A need exists for pharmaceutical agents that can be used to treat osteoporosis. Preferably, such agents will have improved functional activity with minimum adverse side effects.

SUMMARY OF THE INVENTION

The present invention relates to polypeptide analogs which have agonist properties similar to parathyroid hormone or parathyroid hormone-related protein. These polypeptide analogs are useful in the treatment of patients with bone loss. Bone loss may result from conditions such as osteoporosis, glucocorticoid-induced bone loss, hypercortisolism (both subclinical and clinical), cancer, hypercalcemia, renal failure or other kidney disorders, renal transplant and accompanying pharmacological treatments, cholestatic liver diseases, viral hepatitis, bone loss caused by liver transplant, hyperparathyroid disease, bronchial asthma (including hormone-dependent), disorders due to haemodialysis, and osteomalacia. Often bone loss is attributed to idiopathic osteoporosis.

In some aspects of the invention, analogs of parathyroid hormone (PTH) and parathyroid hormone-related protein (PTHrP) are provided. The analogs include shortened forms of human or bovine PTH or human PTHrP polypeptides comprising one or more amino acid substitutions or pseudopeptide units. The amino acid substitutions and pseudopeptide units useful for preparing PTH and/or PTHrP analogs are described in greater detail herein.

According to one aspect of the invention, analogs of PTH or PTHrP that include one or more amino acid substitutions at positions 16, 17, 18, 19 and /or 20 are provided. In preferred embodiments, the amino acid substitutions are $\beta^3$-residues ($\beta$-substituted $\beta$-amino acid residues) although $\beta^2$ -residue substitutions ($\alpha$-substituted $\beta$-amino acid residues) also are provided. In certain preferred embodiments, the analogs include one or more amino acid substitutions selected from the group consisting of:

(a) at position 16: , β-hAsn, β-hSer, β-hGln, β-hThr, β-hAla, β-Ala, β-hRaa, wherein β-hRaa=NH—CH(R) CH$_2$CO, where R=Et, nPr, (CH$_2$)$_n$CONH$_2$ (n=0, 3 and 4);

(b) at position: 17: β-hAsp, β-hSer, β-hGlu, β-hThr, β-hAla, , β-Ala, β-hRaa, wherein β-hRaa=NH—CH(R) CH$_2$CO, where R=Et, nPr, (CH$_2$)$_n$CO$_2$H (n=0, 3 and 4);

(c) at position 18: β-hMet, βhNle, β-hLeu, β-hIle, β-Val, β-hAla, β-Ala, β-hRaa, wherein β-hRaa=NH—CH(R) CH$_2$CO, where R=Et, nPr;

(d) at position 19: β-hAsp, β-hSer, β-hGlu, β-hThr, β-hArg, β-hLys, β-hDap, β-hDbu, β-hOrn, β-hAla, β-Ala, β-hRaa, wherein (β-hRaa=NH—CH(R)CH$_2$CO, where R=(CH$_2$)$_n$Guanidino or guanidine group surrogates (n=1, 2 and 4), (CH$_2$)$_n$CO$_2$H (n=0, 3 and 4); and (e) at position 20: β-hArg, β-hLys, β-hDap, β-hOrn, β-hAla, β-Ala, β-hRaa, wherein β-hRaa=NH—CH(R) CH$_2$CO where R=(CH$_2$)$_n$Guanidino or guanidine group surrogates (n=1, 2 and 4).

Pharmaceutically acceptable salts of the foregoing analogs also are provided.

In certain embodiments, the analogs or pharmaceutically acceptable salts thereof also include one or more of the following amino acid substitutions: Glu at position 22; Leu or 2-Nal at position 23; Glu at position 25; Lys or Aib at position 26; Leu at position 27; Leu at position 28; Glu at position 29; Lys or Leu at position 30; Leu at position 31; Thi at position 32; and Tyr at position 34.

In some preferred embodiments of the foregoing analogs or pharmaceutically acceptable salts thereof, the one or more amino acid substitutions are selected from the group consisting of (β-Ala at position 16, β-Ala or β-hSer at position 17, β-Ala or β-hLeu at position 18, β-Ala or β-hGlu at position 19, and (β-Ala at position 20.

In still other preferred embodiments of the foregoing analogs or pharmaceutically acceptable salts thereof, Nle is substituted for the Met at position 18 in those analogs where there is not a β amino acid at position 18.

In particularly preferred embodiments, the analogs or pharmaceutically acceptable salts thereof include an amino acid sequence set forth as any of SEQ ID NOs:13-41.

Some of the analogs or pharmaceutically acceptable salts thereof provided according to the invention also include a pseudopeptide unit. The pseudopeptide unit preferably is a pseudodipeptide unit comprising $X_{xx}^1\Psi(CH_2NH)Yyy^2$, wherein Xxx is an amino acid selected from the group consisting of Ala, Gly, Thr and Ser, and Yyy is an amino acid selected from-the group consisting of Val, Leu, Nle, Ile and Phe.

According to a second aspect of the invention, analogs of PTH or PTHrP or pharmaceutically acceptable salts thereof that include an amino acid substitution at position 12 and a pseudopeptide unit are provided. The amino acid substituted at position 12 preferably is 2-aminoisobutyric acid (Aib). The pseudopeptide unit preferably is a pseudodipeptide unit comprising $Xxx^1\Psi(CH_2NH)Yyy^2$, wherein Xxx is an amino acid selected from the group consisting of Ala, Gly, Thr and Ser, and Yyy is an amino acid selected from the group consisting of Val, Leu, NMe, Ile and Phe.

In some embodiments of the second aspect of the invention, the analog or pharmaceutically acceptable salt thereof also includes one or more of the following amino acid substitutions: Nle at position 8; Nle at position 18; 2-Nal at position 23; and Tyr at position 34.

In preferred embodiments of the second aspect of the invention, the analog or pharmaceutically acceptable salt thereof includes the amino acid sequence set forth as any of SEQ ID NOs:4, 42 or 43.

According to a third aspect of the invention, analogs of PTH or PTHrP or pharmaceutically acceptable salts thereof are provided that include a set of amino acid substitutions selected from the group consisting of
  set (a): Glu at positions 25 and 29, and Lys 26 and/or 30;
  set (b): Leu at positions 23 and 31, and Leu at position 27 or position 28; and
  set (c): Aib at position 26.

For certain analogs having set (a) amino acid substitutions, the analogs also include one or more of the following amino acid substitutions: Glu at position 22, Leu at positions 23, 27, 28, 30 and 31, and Thi at position 32. In preferred embodiments, the analogs include the amino acid sequence set forth as any of SEQ ID NOs:5, 6, 9, 10 or 12.

For certain analogs having set (b) amino acid substitutions, the analogs also include the amino acid sequence set forth as SEQ ID NO:7 or SEQ ID NO: 11.

For certain analogs having set (c) amino acid substitutions, the analogs also include the amino acid sequence set forth as SEQ ED NO:8.

Any of the foregoing analogs or pharmaceutically acceptable salts thereof can include two or more amino acid substitutions, three or more amino acid substitutions, or four or more amino acid substitutions.

Any of the foregoing analogs or pharmaceutically acceptable salts thereof also can include an amino acid substitution at position 5. Preferably the amino acid substitution at position 5 is His or Ile.

Any of the foregoing analogs or pharmaceutically acceptable salts thereof also can have a modified carboxy terminus. Preferred carboxy terminus modifications include amides or alkylamides.

In preferred embodiments of the foregoing analogs or pharmaceutically acceptable salts thereof, the analog contains fewer amino acids than full-length PTH or PTHrP. Preferably the analog contains between about 30 and about 40 amino acids. More preferably, the analog contains about 34 amino acids.

The invention in another aspect includes pharmaceutical preparations that include any of the foregoing analogs or pharmaceutically acceptable salts thereof, and a pharmaceutically-acceptable carrier.

In another aspect of the invention, methods for treating osteoporosis, promoting bone formation, or inhibiting bone loss in a patient in need of such treatment are provided. The methods include administering an effective amount of the foregoing analogs, pharmaceutically acceptable salts thereof, or pharmaceutical preparations to the patient to treat the osteoporosis, to promote bone formation, or to inhibit bone loss, respectively.

Preferred analogs for use in the methods include bovine PTH analogs including an amino acid sequence as set forth in any of SEQ ID NOs:4, 13-41, human PTH analogs including an amino acid sequence as set forth in SEQ ID NOs: 5-7 or 42, and human PTHrP analogs including an amino acid sequence as set forth in SEQ ID NOs: 8-12 or 43.

In certain embodiments, the foregoing methods also include administering a pharmaceutical agent which is bone resorption inhibiting agent or bone formation promotion agent to the patient. Preferred bone resorption inhibiting agents or bone formation promotion agents include Selective Estrogen-Receptor Modulators (SERMs), estrogens, androgens, cathepsin K inhibitors, calcium supplements, vitamin D (and metabolites and analogs thereof), thiazide diuretics, calcitonin (and analogs thereof), bisphosphonates, fluoride, integrin antagonists, parathyroid hormone, calcilytics, calcimimetics, inhibitors of Src tyrosine kinase and Src SH2 inhibitors.

In other embodiments of the foregoing methods, the analog is administered to the patient at a dosage ranging from 0.1 to 1000 micrograms; preferably the dosage ranges from 20 to 200 micrograms.

In still other embodiments of the foregoing methods, the analog is administered to the patient daily, every second day, every third day, twice per week, every fourth day, every fifth day, every sixth day, or once per week.

Use of the foregoing analogs in the preparation and/or manufacture of a medicament, particularly a medicament for the treatment of osteoporosis, for the promotion of bone formation or for the inhibition of bone loss.

These and other embodiments of the invention are described in greater detail below.

DETAILED DESCRIPTION OF THE INVENTION

Throughout this application, the name of an amino acid may be followed by a superscript number. The superscript number refers to the position of the amino acid in the sequence. For example, Glu22 means there is a glutamic acid at position 22. All polypeptide sequences mentioned herein are written according to the generally accepted convention wherein the N-terminal amino acid is on the left and the C-terminal amino acid is on the right. Numbering starts at the N-terminus and proceeds toward the C-terminus. Accordingly, [Leu$^{23,28,31}$]hPTHrP means a polypeptide having a sequence of hPTHrP in which the wild type residues Phe$^{23}$, Ile$^{28}$, and Ile$^{31}$ have each been replaced with leucine.

As used herein, "hPTH(1-34)" refers to a shortened human sequence of PTH ("hPTH") having amino acids 1 to 34, as set forth in SEQ ID NO:1. Similarly, "bPTH(1-34)" refers to the bovine sequence of PTH ("bPTH") having amino acids 1 to 34, as set forth in SEQ ID NO:2. "hPTHrP(1-34)" refers to a shortened form of human parathyroid hormone related protein ("hPTHrP") having amino acids 1 to 34, as set forth in SEQ ID NO:3.

Preferred polypeptides of the invention include various shortened forms of PTH and PTHrP having amino acid substitutions, i.e., analogs that contain fewer amino acids than full-length PTH or PTHrP. The length of the analogs can be any length that retains activity of PTH or PTHrP, such as binding to a PTH or PTHrP receptor. The shortened analogs can be tested for activity using any of the methods known in the art, some of which are disclosed herein.

The length of the PTH or PTHrP analog can be shortened relative to full-length PTH or PTHrP by 1, 2, 3, 4,5, 6, 7, 8, 9, 10, 11, 12, 13, 14, 15, 16, 17, 18, 19, 20, 21, 22, 23, 24, 25, 26, 27, 28, 30, 31, 32, 33, 34, 35, 36, 37, 38, 39, 40, 41 ,42, 43, 44, 45, 46, 47, 48 ,49, 50 or more amino acids. Preferably the PTH or PTHrP analog contains between about 30 and about 40 amino acids, inclusive (30, 31, 32, 33, 34, 35, 36, 37, 38, 39, 40). Most preferably, the PTH or PTHrP analog contains about 34 amino acids.

The PTH or PTHrP analogs of the invention can be based on PTH or PTHrP sequences of any species, although it is preferred that human PTH or PTHrP or bovine PTH or PTHrP serve as the basis for the analog.

The polypeptides of the invention also encompass analogs that have a modified carboxy terminus. Preferred modified analogs include amidated polypeptides, in which the terminal carboxy group (—COOH) is converted to a carboxamide group (—C(O)NH$_2$). The polypeptides of the invention also can be modified with an alkylamide group.

Therefore, "hPTH(1-34)NH$_2$," as used herein, refers to a truncated form of human parathyroid hormone having a carboxamide group at the carboxy terminus. "bPTH(1-34)NH$_2$," as used herein, refers to a truncated form of bovine parathyroid hormone having a carboxamide group at the carboxy terminus. Similarly, "hPTHrP(1-34)NH$_2$," as used herein, refers to a truncated form of human parathyroid hormone related protein having a carboxamide group at the carboxy terminus.

As used herein, "Ψ(CH$_2$NH)" indicates a reduced peptide bond between two residues. For example, SEQ ID NO:4 has a reduced peptide bond between Ala$^1$ and Val$^2$. As used herein, the amino acid "Nle" is norleucine, "Aib" is 2-aminoisobutyric acid, "2-Nal" is 2-naphthyl-alanine, "Thi" is 2-thienyl-alanine, ",8-Ala" is beta-alanine, "β-hLeu" is beta-homo-leucine, "β-hAsp" is beta-aspartic acid, "β-hSer" is beta-homo-serine, "β-hGlu" is beta-homo-glutamic acid, "β-hThr" is beta-homo-threonine, "β-hArg" is beta-homo-arginine, "β-hLys" is beta-homo-lysine, "β-hDap" is beta-homo-diaminopropionic acid (3,4-diaminobutyric acid), "β-hDbu" is beta-homo-diaminobutyric acid (3,5-diaminopentanoic acid), "β-hOrn" is beta-homo-ornithine., "β-hAla" is beta-homo-alanine, "β-hAsn" is beta-homo-asparagine, and "β-hGln" is beta-homo-glutamine. Thus the invention, in certain aspects, relates preferably to β$^3$-residues (β-substituted β-amino acid residues) but does not exclude β$^2$-residues (α-substituted αamino acid residues). All chiral amino acid residues are of the S-configuration.

In some aspects of the invention, substitutions are made at positions 16-20 of PTH or PTHrP, preferably at positions 17-19. As examples of this, provided below in Table 1 are analogs of bPTH that are substituted at the indicated amino acids. The wild-type bPTH amino acid sequence, SEQ ID NO:2, is provided for comparison. Similar substitutions can be made to hPTH.(SEQ ID NO:1) and to hPTHrP (SEQ ID NO:3), which sequences also are listed for comparison.

Thus β-amino acid-containing analogs can have the following structural permutations, alone or in combination, and optionally with further amino acid substitutions as described elsewhere herein:

Position 16: β-hAsn, β-hSer, β-hGln, β-hThr, β-hAla, β-Ala, β-hRaa, wherein β-hRaa=NH—CH(R)CH$_2$CO, where R=Et, nPr, (CH$_2$)$_n$CONH$_2$(n=0, 3 and 4).

Position 17: β-hAsp, β-hSer, β-hGlu, β-hThr, β-hAla, β-Ala, β-hRaa, wherein β-hRaa=NH—CH(R)CH$_2$CO, where R=Et, nPr, (CH$_2$)$_n$CO$_2$H (n=0, 3 and 4).

Position 18: β-hMet, β-hNle, β-hLeu, β-hIle, βhVal, β-hAla, β-Ala, β-hRaa, wherein β-hRaa=NH—CH(R)CH$_2$CO, where R=Et, nPr.

Position 19: β-hAsp, β-hSer, β-hGlu, β-hThr, β-hArg, β-hLys, β-hDap, β-hDbu, β-hOrn, β-hAla, β-Ala, β-hRaa, wherein β-hRaa=NH—CH(R)CH$_2$CO, where R=(CH$_2$)$_n$ Guanidino or guanidine group surrogates (n=1, 2 and 4), (CH$_2$)$_n$CO$_2$H (n=0, 3 and 4).

Position 20: β-hArg, β-hLys, β-hDap, β-hOrn, β-hAla, β-Ala, β-hRaa, wherein β-hRaa=NH—CH(R)CH$_2$CO where R=(CH$_2$)$_n$Guanidino or guanidine group surrogates (n=1, 2 and 4).

Preferred substitutions include βamino acids β-Ala at position 16, β-Ala or β-hSer at position 17, β-Ala or β-hLeu at position 18, β-Ala or β-hGlu at position 19, and β-Ala at position 20, as shown in the examplary analogs presented in Table 1. Norleucine (Nle) is preferably substituted for the methionine (Met) at position 18 in those analogs where there is not a βamino acid at position 18. Guanidine group surrogates include the following molecules:

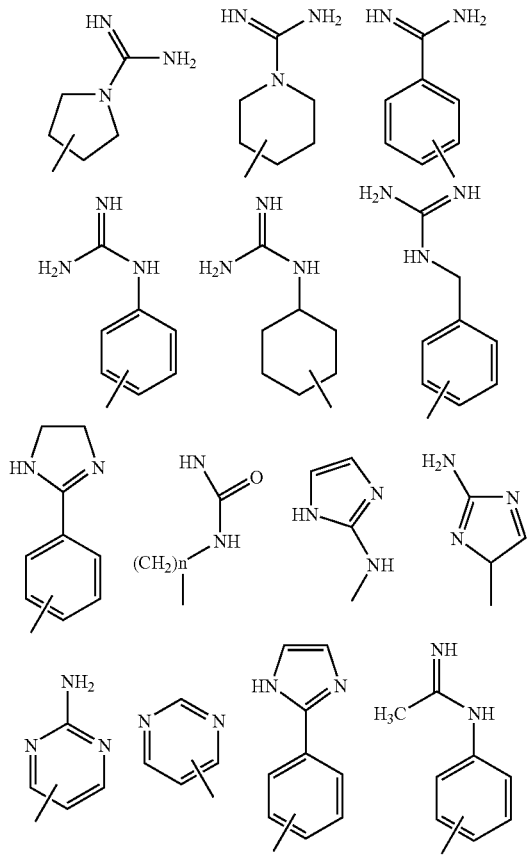

-continued

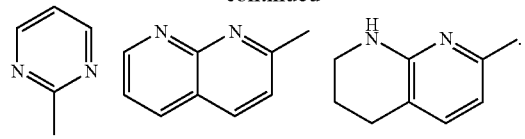

TABLE 1

Exemplary amino acid substitutions of bPTH

| PTH/PTHrP/Analog Amino Acid Sequence | SEQ ID NO |
|---|---|
| SVSEIQLMHNLGKHLNSMIERVEWLRKKLQDVHNF | 1 (hPTH) |
| AVSEIQFMHNLGKHLSSMERVEWLRKKLQDVHNF | 2 (bPTH) |
| AVSEHQLLHDKGKSIQDLRRRFFLHHLIAEIHTA | 3 (hPTHrP) |
| AVSEIQFMHNLGKHL-β-Ala$^{16}$-Ser-Nle-Glu-RVEWLRKKLQDVHNF | 18 |
| AVSEIQFMHNLGKHLS-Ser-Nle-Glu-β-Ala$^{20}$-VEWLRKKLQDVHNF | 19 |
| AVSEIQFMHNLGKHLS-β-Ala$^{17}$-Nle-Glu-RVEWLRKKLQDVHNF | 20 |
| AVSEIQFMHNLGKHLS-Ser-β-Ala$^{18}$-Glu-RVEWLRKKLQDVHNF | 21 |
| AVSEIQFMHNLGKHLS-Ser-Nle-β-Ala$^{19}$-RVEWLRKKLQDVHNF | 22 |
| AVSEIQFMHNLGKHLS-β-hSer$^{17}$-Nle-Glu-RVβWLRKKLQDVKNF | 23 |
| AVSEIQFMHNLGKHLS-Ser-β-hLeu$^{18}$-Glu-RVEWLRKKLQDVHNF | 24 |
| AVSEIQFMHNLGKHLS-Ser-Nle-β-hGlu$^{19}$-RVEWLRKKLQDVHNF | 25 |
| AVSEIQFMHNLGKHLS-β-Ala$^{17}$-β-Ala$^{18}$-Glu-RVEWLRKKLQDVHNF | 26 |
| AVSEIQFMHNLGKHLS-Ser-β-Ala$^{18}$-β-Ala$^{19}$-RVEWLRKKLQDVHNF | 27 |
| AVSEIQFMHNLGKHLS-β-Ala$^{17}$-Nle-β-Ala$^{19}$-RVEWLRKKLQDVHNF | 28 |
| AVSEIQFMHNLGKHLS-β-Ala$^{17}$-β-hLeu$^{18}$-Glu-RVEWLRKKLQDVHNF | 29 |
| AVSEIQFMHNLGKHLS-Ser-β-hLeu$^{18}$-β-Ala$^{19}$-RVEWLRKKLQDVENF | 30 |
| AVSELQFMHNLGKHLS-Ser-β-Ala$^{18}$-β-hGlu$^{19}$-RVEWLRKKLQDVHNF | 31 |
| AVSEIQFMHNLGKHLS-β-Ala$^{17}$-Nle-β-hGlu$^{19}$-RVEWLRKKLQDVHNF | 32 |
| AVSEIQFMHNLGKHLS-β-hSer$^{17}$-Nle-β-Ala$^{19}$-RVEWLRKKLQDVHNF | 33 |
| AVSEIQFMHNLGKHLS-β-hSer$^{17}$-Nle-β-Ala$^{19}$-Glu-RVEWLRKKLQDVHNF | 34 |
| AVSEIQFMHNLGKHLS-β-hSer$^{17}$-β-Ala$^{18}$-β-Ala$^{19}$-RVEWLRKKLQDVHNF | 35 |
| AVSEIQFMHNLGKHLS-β-Ala$^{17}$-β-Ala$^{18}$-β-hGlu$^{19}$-RVEWLRKKLQDVHNF | 36 |
| AVSEIQFMHNLGKHLS-β-Ala$^{17}$-β-hLeu$^{18}$-β-Ala$^{19}$-RVEWLRKKLQDVHNF | 37 |
| AVSEIQFMHNLGKHLS-β-hSer$^{17}$-β-hLeu$^{18}$-Glu-RVEWLRKKLQDVHNF | 38 |
| AVSEIQFMHNLGKHLS-Ser-β-hLeu$^{18}$-β-hGlu$^{19}$-RVEWLRKKLQDVHNF | 39 |
| AVSEIQFMHNLGKHLS-β-hSer$^{17}$-Nle-β-hGlu$^{19}$-RVEWLRKKLQDVHNF | 40 |
| AVSEIQFMHNLGKHLS-β-hSer$^{17}$-β-hLeu-β-hGlu$^{19}$-RVEWLRKKLQDVHNF | 41 |

As described in the examples below, one set of preferred analogs of h/bPTH and hPTHrP include the following analogs:

TABLE 2

Exemplary PTH/PTHrP Analogs

| SEQ ID NO: | ANALOG AMINO ACID SEQUENCE |
|---|---|
| 5 | [Glu$^{25,29}$, Leu$^{23,27,31}$, Lys$^{30}$]hPTH(1-34)NH$_2$ |
| 6 | [Glu$^{25,29}$, Lys$^{30}$]hPTH(1-34)NH$_2$ |
| 7 | [Leu$^{23,27,31}$]hPTH(1-34)NH$_2$ |
| 8 | [Aib$^{26}$]hPTHrP(1-34)NH$_2$ |
| 9 | [Glu$^{22,25,29}$, Leu$^{23,28,31}$, Lys$^{26,30}$, Thi$^{32}$]hPTHrP(1-34)NH$_2$ |
| 10 | [Glu$^{22,25,29}$, Leu$^{23,28,30,31}$, Lys$^{26}$]hPTHrP(1-34)NH$_2$ |
| 11 | [Leu$^{23,28,31}$]hPTHrP(1-34)NH$_2$ |
| 12 | [Glu$^{22,25,29}$, Lys$^{26,30}$]hPTHrP(1-34)NH$_2$ |
| 13 | [Nle$^8$, β-Ala$^{18}$, Nal$^{23}$, Tyr$^{34}$]bPTH(1-34)NH$_2$ |
| 14 | [Nle$^8$, β-Ala$^{18,19}$, Nal$^{23}$, Tyr$^{34}$]bPTH(1-34)NH$_2$ |
| 15 | [Nle$^{8,18}$, β-Ala$^{19}$, Nal$^{23}$, Tyr$^{34}$]bPTH(1-34)NH$_2$ |
| 16 | [Nle$^8$, β-hLeu$^{18}$, β-Ala$^{19}$, Nal$^{23}$, Tyr$^{34}$]bPTH(1-34)NH$_2$ |
| 17 | [Nle$^8$, β-Ala$^{17,19}$, β-hLeu$^{18}$, Nal$^{23}$, Tyr$^{34}$]bPTH(1-34)NH$_2$ |

Additional examples of structural permutations in analogs of h/bPTH and hPTHrP include analogs having one or more pseudopeptide units. Preferred pseudopeptide units include pseudodipeptide units, pseudotripeptide units, pseudotetrapeptide units, etc., which can be located at any series of amino acids in the h/bPTH and hPTHrP analogs. In some preferred embodiments, the pseudodipeptide unit Xxx$^1$Ψ(CH$_2$NH)Yyy$^2$ can be one of the following: Xxx=Ala, Gly, Thr, Ser and Yyy=Val, Leu, Me, Ile, Phe. In certain embodiments, analogs containing a pseudodipeptide unit also contain a 2-aminoisobutyric acid residue substitution at position 12 (Aib$^{12}$). Exemplary analogs containing a pseudodipeptide unit include the following:

[Ala$^1$Ψ(CH$_2$NH)Val$^2$, Nle$^{8,18}$, Aib$^{12}$, 2-Nal$^{23}$, Tyr$^{34}$]bPTH(1-34)NH$_2$ (SEQ ID NO:4)

[Ser$^1$Ψ(CH$_2$NH)Val$^2$, Nle$^{8,18}$, Aib$^{12}$, 2-Nal$^{23}$, Tyr$^{34}$]hpTH(1-34)NH$_2$ (SEQ ID NO:42)

[Ser$^1$Ψ(CH$_2$NH)Val$^2$, Aib$^{12}$]hpTHrP(1-34)NH$_2$ (SEQ ID NO:43).

In further embodiments, hPTH, bPTH and hPTHrP analogs contain additional or different amino acid substitutions. For example, instead of the substituted Glu residues mentioned above, one can introduce Asp, or NHCH(R)CO, where R is (CH$_2$)$_n$CO$_2$H and n=0, 3 and 4. Instead of the substituted Leu residues mentioned above one can introduce Nle, Ile, Val, Ala, Met, or NHCH(R)CO, where R is Et, or nBu. Instead of the substituted Lys residues mentioned above one can introduce Dap, Dbu, or NHCH(R)CO where R is (CH$_2$)$_n$NH$_2$ and n=5-7.

In still other embodiments, the analogs described herein also can include an amino acid substitution at position 5, preferably a His or Ile substitution. Such substitutions are known to influence binding of PTH and PTHrP to their receptors (see, e.g., Behar et al., Endocrinology 137:4217-4224, 1996). Exchanging between Ile and His in position 5 of PTH and PTHrP, respectively, modifies sub-type receptor specificity. His$^5$-PTH becomes less favorable at the PTH2-Rc compared to parent PTH and Ile$^5$-PTHrP becomes more favorable at the PTH1-Rc compared to the parent PTHrP. Preferred PTH/PTHrP analogs targeted for bone anabolic treatment have increased selectivity toward the PTH1-Rc located at bone and kidney, the target tissues for PTH. Hence, substitution of PTH-derived analogs with His at position 5 is anticipated to increase favorably their affinity and avidity to the PTH1-Rc.

The polypeptides of the invention have several uses, including, but not limited to, treating osteoporosis, promoting bone formation, and inhibiting bone loss. Additionally, the polypeptides of the invention may be used to treat glucocorticoid-induced bone loss, hypercortisolism (both subclinical and clinical), cancer, hypercalcemia, renal failure or other kidney disorders, renal transplant and accompanying pharmacological treatments, cholestatic liver diseases, viral hepatitis, liver disorders caused by liver transplant, hyperparathyroid disease, bronchial asthma (including hormone-dependent), disorders due to haemodialysis, and osteomalacia. In such settings, the polypeptides of the invention are administered to patients in need of such treatments in effective amounts.

Patients include men, women, children, young adults, adults, and elderly adults. An important group of patients includes post-menopausal women.

The polypeptides of the invention are administered in effective amounts. An effective amount means that amount necessary to delay the onset of, inhibit the progression of, halt altogether the onset or progression of, or diagnose the particular condition being treated. When administered to a subject, effective amounts will depend on the particular condition being treated, the severity of the condition, individual patient parameters including age, sex, physical condition, size and weight, concurrent treatment, frequency of treatment, and the mode of administration. These factors are well known to those of ordinary skill in the art and can be addressed with no more than routine experimentation. It is preferred generally that a maximum dose be used, that is, the highest safe dose according to some medical judgment.

As used herein, "treating osteoporosis" means that the patient's bone density increases, remains the same, or does not decrease as rapidly as it would without the administration of a polypeptide of the invention. Generally, it is preferable that the patient's bone density remains the same or increases. More preferably, the patient's bone density increases by about 1%, 5%, 10%, or more.

As used herein, "promoting bone formation" means that bone density increases by about 1%, 5%, 10%, or more.

In particularly preferred embodiments of the foregoing methods, bone density will increase by 5-10% in 12-18 months of treatment.

As used herein, "inhibiting bone loss" means that the patient's bone density remains the same, or does not decrease as rapidly as it would without the compounds of the invention. Preferably, the patient's bone density decrease is inhibited by about 85%, 90%, 95%, 99%, or more.

When determining the rate of change or amount of change in bone density, patients may serve as their own controls, or their bone densities may be compared to statistically-derived levels, determined, for example, by clinical trials. One such trial is described by Neer et al. (*N. Engl. J. Med.* 344:1434-1441, 2001).

Bone density is easily measured using routine methods known to those of skill in the art. For example, see Neer et al. (*N. Engl. J. Med.* 344:1434-1441, 2001), which provides exemplary methods for analysis the effect of the administration of PTH and/or PTHrP analogs. Other methods for measuring bone density will be known to one of ordinary skill in the art.

When administered, pharmaceutical preparations of the invention are applied in pharmaceutically acceptable amounts and in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, p-toluenesulfonic, tartaric, citric, methanesulfonic, formic, succinic, naphthalene-2-sulfonic, pamoic, 3-hydroxy-naphthalenecarboxylic, and benzene sulfonic. Also, pharmaceutically acceptable salts can be prepared as alkaline metal or alkaline earth salts, such as sodium, ammonium, magnesium, potassium or calcium salts of the carboxylic acid group.

Suitable buffering agents include: acetic acid and salts thereof (1-2% W/V); citric acid and salts thereof (1-3% W/V); boric acid and salts thereof (0.5-2.5% W/V); and phosphoric acid and salts thereof (0.8-2% W/V).

Suitable preservatives include benzalkonium chloride (0.003-0.03% W/V); chlorobutanol (0.3-0.9% W/V); parabens (0.01-0.25% W/V) and thimerosal (0.004-0.02% W/V).

A variety of administration routes are available. The particular mode selected will depend, of course, upon the particular combination of therapeutic agents selected, the severity of the condition or disorder being treated, or prevented, the condition of the patient, and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, transdermal, sublingual or intramuscular, infusion, parenteral, intravenous, intramuscular, intracavity, as a feed additive, as an aerosol, buccal, aural (e.g., via eardrops), intranasal, inhalation, or subcutaneous. Direct injection could also be preferred for local delivery to the site of injury.

Although at present subcutaneous administration is routinely employed in the administration of PTH and/or PTHrP, oral administration may be preferred for treatment because of the convenience of the subject (patient) as well as the dosing schedule. Generally, daily oral doses of active compounds will be from about 0.1 microgram per day to 1000 micrograms per day. It is expected that oral doses in the range of 0.5 to 50 micrograms, in one or several administrations per day, will yield the desired results. Dosage may be adjusted appropriately to achieve desired drug levels, local or systemic, depending upon the mode of administration. For example, it is expected that intravenous administration would be from an order to several orders of magnitude lower dose per day compared to the oral doses. In the event that the response in a subject is insufficient at such doses, even higher doses (or effective higher doses by a different, more localized delivery route) may be employed to the extent that patient tolerance permits.

Preferably the polypeptides of the invention are administered intermittently, which is known in the art to promote anabolic efficacy of PTH, PTHrP and its analogs. Preferred intermittent administration schedules include daily, every second day, every third day, twice per week, every fourth day, every fifth day, every sixth day, and once per week.

The compositions may conveniently be presented in unit dosage form and may be prepared by any of the methods well known in the art of pharmacy. All methods include the step of bringing the compounds of the invention into association with a carrier which constitutes one or more accessory ingredients. In general, the compositions are prepared by uniformly and intimately bringing the compounds of the invention into association with a liquid carrier, a finely divided solid carrier, or both, and then, if necessary, shaping the product.

Compositions suitable for parenteral administration conveniently comprise a sterile aqueous preparation of the compounds of the invention is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. are well known in the art.

Compositions suitable for oral administration may be presented as discrete units such as capsules, cachets, tablets, syrups, elixirs or lozenges, each containing a predetermined amount of the compounds of the invention. Compositions suitable for any pulmonary delivery typically are formulated and/or are contained in a nebulizer.

Other delivery systems can include time-release, delayed release or sustained release delivery systems. Such systems can avoid repeated administrations of the compounds of the invention, increasing convenience to the subject and the physician, yet are constructed to provide the anabolic benefit of the polypeptides of the invention. Many types of release delivery systems are available and known to those of ordinary skill in the art. They include polymer based systems such as polylactic and polyglycolic acid, polyanhydrides and polycaprolactone, nonpolymer systems that are lipids including sterols such as cholesterol, liposomes; phoshpholipids; hydrogel release systems; silastic systems; peptide based system; implants and the like. Specific examples include, but are not limited to: (a) erosional systems in which the polypeptide is contained in a form within a matrix, found in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based delivery systems can be used, some of which are adapted for implantation.

Use of a long-term sustained release implant may be particularly suitable for treatment of chronic conditions.

"Long-term" release, as used herein, means that the implant is constructed and arranged to deliver therapeutic levels of the active ingredient for at least 7 days, preferably for 30-60 days and more preferably for longer periods of time (e.g., 12 months or longer). The implant may be positioned at a site of injury, but need not be. Long-term sustained release implants are well-known to those of ordinary skill in the art and include some of the release systems described above. One such implant system is described in U.S. Pat. No. 6,159,490.

The polypeptides of the invention may be delivered with other agents for treating osteoporosis, agents for promoting bone formation, and/or agents for inhibiting bone loss or individually, yet close enough in time to have a synergistic effect on the treatment.

EXAMPLES

Example 1

Synthesis of the Polypeptides of the Invention

Peptides were synthesized by the solid-phase methodology (Merrifield, R. B. *J. Am. Chem. Soc.* 1963, 85, 2149-2154) on an Applied Biosystems 430A peptide synthesizer using Boc/HOBt/NMP chemistry and p-methylbenzhydrylamine.HCl resin. General protocols for the synthesis, purification and characterization of peptides were reported elsewhere (Zhou, A. T.; Besalle, R.; Bisello, A.; Nakamoto, C.; Rosenblatt, M.; Suva, L. J.; Chorev, M. Proc. Natl. Acad. Sci. USA 1997, 94, 3644-3649; Bisello, A.; Adams, A.; Mierke, D.; Pellegrini, M.; Rosenblatt, M.; Suva, L.; Chorev, M. J. Biol. Chem. 1998, 273, 22498-22505; Nakamoto, C.; Behar, V.; Chin, K. R.; Adams, A. E.; Suva, L. J.; Rosenblatt, M.; Chorev, M. Biochemistry 1995, 34, 10546-10552; Goldman, M. E.; Chorev, M.; Reagan, J. E.; Nutt, R. F.; Levy, J. J.; Rosenblatt, M. Endocrinology 1988, 123, 1468-1475). Specifically, the synthesis was carried out on a 0.5-mmol scale. The resin-bound side chain protected Boc[Tyr$^{34}$]PTH(25-34) was split into two halves and the stepwise synthesis continued to generate resin-bound side chain protected Boc[Nle$^{18}$, Nal$^{23}$, Tyr$^{34}$]PTH(14-34). At this point the synthesis resumed with aliquots of 0.05 mmol of resin-bound fully protected 21-residue peptide which was carried out to the completion of the full sequence. The protocol included double couplings, followed by capping with Ac$_2$O, for the following positions: Ile$^5$, Gln$^6$, Phe$^7$, His$^8$, Lys$^{13}$, His$^{14}$, Leu$^{15}$, Xxx$^{18}$, Yyy$^{19}$, Arg$^{20}$, Val$^{21}$, Leu$^{22}$, Arg$^{21}$, Glu$^{22}$, Nal$^{23}$, Leu$^{24}$ and Val$^{31}$ (Xxx and Yyy represent either the native residues, Met and Glu, respectively, or the corresponding beta-amino acid residues). After hydrogen fluoride cleavage, the peptides were purified by preparative reversed-phase high performance liquid chromatography (RP-HPLC) employing a Vydac® Protein C18 column (300 Å, 15-20 μm, 57×300 mm, Waters, Milford, Mass.). The elution was carried out employing a linear gradient of 0-15% B for 10 min followed by 15-50% B for 120 min (A=0.1% TFA in water; B=0.1% TFA in acetonitrile) at a flow rate of 70 mL/min and monitored at 220 nm. Purity exceeded 97% as determined by analytical RP-HPLC. Structural integrity of the peptides was confirmed by amino acid analysis and electrospray mass spectrometry.

Example 2

Determination of IC$_{50}$

SaOS-2/B10 cells were maintained in RPMI1640 medium supplemented with 10% fetal bovine serum (FBS) and 2 mM glutamine at 37° C. in a humidified atmosphere of 5% CO$_2$ in air. The medium was changed every three to four days, and the cells were subcultured every week by trypsinization.

SaOS-2/B10 cells were maintained for four days after they had reached confluence. The medium was replaced with 5% FBS RPS/1640 medium and incubated for 2 hrs at room temperature with 10×10$^4$ cpm mono-$^{125}$I-[Nle$^{8,18}$,Tyr$^{34}$(3-$^{125}$I)]bPTH(1-34)NH$_2$ in the presence or absence of a competing tested polypeptide of the invention. The cells were washed four times with ice-cold PBS and lysed with 0.1M NaOH, and the radioactivity associated with the cells was counted in a scintillation counter. Synthesis of the radiolabelled [Nle$^{8,18}$,Tyr$^{34}$(3-$^{125}$I)]bPTH(1-34)NH$_2$ was carried out as described in Goldman M. E., et al., *Endocrinology*, (1988), 123, 1468-1475.

The binding assay was conducted on the polypeptides of the invention having SEQ ID NO:5, 6, 7, 9, 10, 11, and 12. The IC$_{50}$s (half maximal inhibition of binding of mono-$^{125}$I-[Nle$^{8,18}$,Tyr$^{34}$(3-$^{125}$I)]bPTH(1-34)NH$_2$) for the tested analogs were calculated and shown in Table 3 below:

TABLE 3

IC$_{50}$ of certain-hPTH/hPTHrP analogs

| Sequence | Description | IC$_{50}$ (nM) |
|---|---|---|
| SEQ ID NO: 5 | [Glu$^{25,29}$, Leu$^{23,27,31}$, Lys$^{30}$]hPTH(1-34)NH$_2$ | 216 |
| SEQ ID NO: 6 | [Glu$^{25,29}$, Lys$^{30}$]hPTH(1-34)NH$_2$ | 30 |
| SEQ ID NO: 7 | [Leu$^{23,27,31}$]hPTH(1-34)NH$_2$ | 41 |
| SEQ ID NO: 9 | [Glu$^{22,25,29}$, Leu$^{23,28,31}$, Lys$^{26,30}$, Thi$^{32}$]hPTHrP(1-34)NH$_2$ | 90 |
| SEQ ID NO: 10 | [Glu$^{22,25,29}$, Leu$^{23,28,30,31}$, Lys$^{26}$]hPTHrP(1-34)NH$_2$ | 70 |
| SEQ ID NO: 11 | [Leu$^{23,28,31}$]hPTHrP(1-34)NH$_2$ | 18.3 |
| SEQ ID NO: 12 | [Glu$^{22,25,29}$, Lys$^{26,30}$]hPTHrP(1-34)NH$_2$ | 5.5 |

Example 3

Determination of Stimulation of Adenylate Cyclase Activity

The adenylate cyclase activity induced by each of the tested polypeptides of the invention was also measured in SaOS-2/B 10 cells as described previously (Rodain et al., *J. Clin. Invest.* (1983) 72,1511; Goldman, et al., *Endocrinology* (1988) 123, 1468). Conflúnt SaOS-2/B10 cells in 24 wells plates were incubated with 0.5 µCi [$^3$H]adenine (26.9 Ci/mmol, New England Nuclear, Boston, Mass. in fresh medium at 37° C. for 2 hrs. and washed twice with Hank's solution. The cells were treated with 1 mM IBMX (isobutylmethylxanthine, Sigma, St. Louis, Mo.) in fresh medium for 15 min. and a tested PTH analog was added to the medium to incubate for 5 min. The reaction was stopped by the addition of 1.2M TCA followed by sample neutralization with 4N KOH. Cyclic AMP was isolated by the two-column chromatographic method (Salomon, et al., *Anal. Biochem.* (1974) 58, 541). The radioactivity was counted in a scintillation counter (Liquid scintillation counter 2200CA, PACKARD, Downers Grove, Ill.). The $EC_{50}$s (half maximal stimulation of adenylate cyclase) were calculated for the tested PTH analogs and are shown in Table 4 below:

TABLE 4

$EC_{50}$ of certain hPTH/hPTHrP analogs

| Sequence | Description | $EC_{50}$(nM) |
|---|---|---|
| SEQ ID NO: 5 | [Glu$^{25,29}$, Leu$^{23,27,31}$, Lys$^{30}$]hPTH(1-34)NH$_2$ | 24 |
| SEQ ID NO: 6 | [Glu$^{25,29}$, Lys$^{30}$]hPTH(1-34)NH$_2$ | 25.5 |
| SEQ ID NO: 7 | [Leu$^{23,27,31}$]hPTH(1-34)NH$_2$ | 1.12 |
| SEQ ID NO: 9 | [Glu$^{22,25,29}$, Leu$^{23,28,31}$, Lys$^{26,30}$,Thi$^{32}$]hPTHrP(1-34)NH$_2$ | 10 |
| SEQ ID NO: 10 | [Glu$^{22,25,29}$, Leu$^{23,28,30,31}$, Lys$^{26}$]hPTHrP(1-34)NH$_2$ | 5 |
| SEQ ID NO: 11 | [Leu$^{23,28,31}$]hPTHrP(1-34)NH$_2$ | 0.74 |
| SEQ ID NO: 12 | [Glu$^{22,25,29}$, Lys$^{26,30}$]hPTHrP(1-34)NH$_2$ | 0.42 |

Example 4

Determination of $IC_{50}$

Human embryonic kidney (HEK293) cells, stably transfected with recombinant hPTH1-receptor (HEK293/C21 cell line, ~400,000 receptors/cell) (Pines, M., Adams, A. E., Stueckle, S., Bessalle, R., Rashti-Behar, V., Chorev, M., Rosenblatt, M., and Suva, L. J. Endocrinology 1994, 135, 1713-1716), were maintained in D-MEM medium supplemented with 10% fetal bovine serum and 2 nM glutamine at 37° C. in a humidified atmosphere of 95% air/5% CO$_2$. The medium was changed every 3-4 days, and the cells were subcultured every week. Ligand stimulated adenylyl cyclase activity and radioreceptor competition binding assays were performed on confluent cultures, 1-3 days after a change of medium.

[Nle$^{8,18}$,Nal$^{23}$,Tyr$^{34}$]bPTH(1-34)-NH$_2$ was radioiodinated and the crude material was purified as previously described (Roubini, E., Duong, L. T., Gibbons, S. W., Leu, C. T., Caulfield, M. P., Chorev, M., and Rosenblatt, M. Biochemistry 1992, 31, 4026-4033). Briefly, 67 µg of peptide in 50 µL phosphate buffer, pH 7.4, in a borosilicate tube, coated with 10 µg Iodogen® (Pierce Chemical), were treated at room temperature with 2 mCi [$^{125}$I]Na for 12 min, followed by dilution with 200 µL of 0.1% TFA in water. The pure mono-radioiodinated peptide was isolated on an analytical RP-HPLC Vydac Protein C18 column (The Separation Group, Hesperia, Calif.) employing a linear gradient of 36-42% B in A for 30 min (A, 0.1% TFA in water; B, 0.1% TFA in acetonitrile) at a flow rate of 1 mL/min, and monitored at 220 nm.

Cells were plated in 24-well tissue culture dishes (Corning Glass Works, Corning, N.Y.) and grown to subconfluency. The cells were then incubated for 2 h at room temperature in fresh PBS supplemented medium (0.25 mL) containing 100,000 cpm (~0.1 nM) of the mono-radioiodinated ligand 125I-PTH(1-34) in the absence or presence of increasing concentrations of unlabeled competing ligand. After incubation, cells were washed twice with PBS and lysed with 0.1 M NaOH. Radioactivity in the lysate was measured in a γ-counter (Analytic GammaTrac™ 1193). The IC50s for the tested analogs were calculated and shown in Table 5 below:

TABLE 5

$IC_{50}$ of certain bPTH analogs

| Sequence | Description | $IC_{50}$(nM) |
|---|---|---|
| SEQ ID NO: 13 | [Nle$^8$,β-Ala$^{18}$, Nal$^{23}$, Tyr$^{34}$]bPTH(1-34)NH$_2$ | 285 ± 85 |
| SEQ ID NO: 14 | [Nle$^8$, β-Ala$^{18,19}$, Nal$^{23}$, Tyr$^{34}$]bPTH(1-34)NH$_2$ | >1000 |
| SEQ ID NO: 15 | [Nle$^{8,18}$, β-Ala$^{19}$, Nal$^{23}$, Tyr$^{34}$]bPTH(1-34)NH$_2$ | 59 ± 7 |
| SEQ ID NO: 16 | [Nle$^8$, β-hLeu$^{18}$, β-Ala$^{19}$, Nal$^{23}$, Tyr$^{34}$]bPTH(1-34)NH$_2$ | 117 ± 19 |
| SEQ ID NO: 17 | [Nle$^8$, β-Ala$^{17,19}$, β-hLeu$^{18}$, Nal$^{23}$, Tyr$^{34}$]bPTH(1-34)NH$_2$ | >1000 |

Example 5

Determination of Stimulation of Adenylate Cyclase Activity

Stimulation of adenylyl cyclase activity by the PTH(1-34) analogues was assayed in stably transfected HEK293/C21 as described before (Nakamoto, C., Behar, V., Chin, K. R., Adams, A. E.; Suva, L. J.; Rosenblatt, M.; Chorev, M. Biochemistry 1995, 34, 10546-10552.). Shortly, cells were grown to confluence in 24-well culture dishes. They were then incubated with 0.5 μCi [$^3$H]adenine in fresh PBS supplemented medium at 37° C. for 2 h and further treated with 1 mM 3-isobutyl-1-methylxantine (IBMX) in fresh medium for 15 min at 37° C. This treatment was followed by 5 min incubation with the corresponding analogue. The reaction was terminated by adding 1.2 M trichloroacetic acid and neutralized with 4 N KOH. cAMP was isolated by the two-column chromatographic method (Solomon, Y., Londos, C., and Rodbell, M. A. Anal. Biochem. 1974, 58, 541-548). Radioactivity was measured in a liquid scintillation counter (Beciman LS6000IC liquid scintillation counter, Downers Grove, Ill.). The $EC_{50}$s (half maximal stimulation of adenylate cyclase) were calculated for the tested PTH analogs and are shown in Table 6 below:

TABLE 6

$EC_{50}$ of certain bPTH analogs

| Sequence | Description | $EC_{50}$(nM) |
|---|---|---|
| SEQ ID NO: 13 | [Nle$^8$, β-Ala$^{18}$, Nal$^{23}$, Tyr$^{34}$]bPTH(1-34)NH$_2$ | 3.90 ± 0.22 |
| SEQ ID NO: 14 | [Nle$^8$, β-Ala$^{18,19}$, Nal$^{23}$, Tyr$^{34}$]bPTH(1-34)NH$_2$ | 13.82 ± 0.02 |
| SEQ ID NO: 15 | [Nle$^{8,18}$, β-Ala$^{19}$, Nal$^{23}$, Tyr$^{34}$]bPTH(1-34)NH$_2$ | 1.51 ± 0.21 |
| SEQ ID NO: 16 | [Nle$^8$, β-hLeu$^{18}$, β-Ala$^{19}$, Nal$^{23}$, Tyr$^{34}$]bPTH(1-34)NH$_2$ | 2.73 ± 0.31 |
| SEQ ID NO: 17 | [Nle$^8$, β-Ala$^{17,19}$, β-hLeu$^{18}$, Nal$^{23}$, Tyr$^{34}$]bPTH(1-34)NH$_2$ | 9.97 ± 1.03 |

Example 6

Determination of In Vivo Bone Anabolic Activity

In vivo bone anabolic activities of the polypeptides of the invention are tested by administering the peptide of a formulation containing the peptide into intact animals or an experimental animal model of osteopenia. The ovariectomized rat is an established animal model for osteoporosis (Hori, M., et al., *Bone Miner.*, (1988), 3, 193-199; Geral, et al., *J. Bone Miner. Res.*, (1989) 4, Supp. 1, S303; Liu, C-C, et al., *J. Bone Miner. Res.* (1990), 5, 973-982; Mosekilde, L, et al., *Endocrinol.*, (1991), 129, 421-428; Wronski, T. J., et al, *Bone*, (1994), 15, 51-58; Reviewed in Demster D. W., et al., *Endocrine Rev.*, (1993), 14, 690-709).

The bone anabolic effects of the compound are determined following 12 to 60 days of treatment by assessing the change in bone mineral density by dual energy x-ray absorptiometry or dry weight of femurs or total ash weight (Hori, H., et al., *Bone Miner.*, (1988), 3, 193-199; Hefti, E., et al., *Clin. Sci.* (1982), 62, 389-396). Increase in the rate of bone formation and mineralization are assessed using metabolic labels, e.g., tetracycline (Tam, C. S., et al., Endocriniology, (1982), 110, 506-512). Qualitative and quantitative evaluations of changes in trabecular/cortical bone volume and complexity are determined by standard histomorphometric analysis (Wronski, T. J., et al., *Bone*, (1994), 15, 51-58; Tam, C. S., et al., *Endocrinology* (1982), 110, 506-612; Podbesek, R., et al., *Endocrinology* (1983), 112, 1000-1006) of bone samples from control (untreated) and treated animals.

Each of the patents, patent applications and references that are recited in this application are herein incorporated in their entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

What is claimed is:

1. An analog of PTH comprising an amino acid substitution: at position 16 of SEQ ID NO: 1 selected from the group consisting of β-hAsn, β-hSer, β-hGln, β-hThr, β-hAla, β-Ala, β-hRaa, wherein β-hRaa=NH—CH(R)CH$_2$CO, where R=Et, nPr, (CH$_2$)nCONH$_2$ (n=0, 3 and 4) or a pharmaceutically acceptable salt thereof, the analog of PTH optionally further comprising one or more amino acid substitutions at positions 1, 5, 7, 18, 23, 25, 26, 27, 29, 30, 31, 32 and 34; and/or optionally comprising a reduced peptide bond; and/or optionally comprising a modification at the carboxy terminus.

2. The analog or pharmaceutically acceptable salt thereof of claim 1, wherein the one or more amino acid substitutions at positions 1, 5, 7, 18, 23, 25, 26, 27, 29, 30, 31, 32 and 34 are selected from the following amino acid substitutions: Ala at position 1: His at position 5; Phe at position 7: Leu, Nle, β-Ala, β-hLeu at position 18: Leu or 2-Nal at position 23; Glu at position 25; Aib at position 26; Leu at position 27, Glu at position 29; Lys or Leu at position 30; Leu at position 31; Thi at position 32; and Tyr at position 34.

3. The analog or pharmaceutically acceptable salt thereof of claim 1, wherein the amino acid substitution is β-Ala at position 16.

4. The analog or pharmaceutically acceptable salt thereof of claim 1, wherein the analog comprises the amino acid sequence set forth as SEQ ID NO:18.

5. The analog or pharmaceutically acceptable salt thereof of claim 1, wherein the analog comprises a reduced peptide bond between two residues Xxx and Yyy, and wherein Xxx is an amino acid selected from the group consisting of Ala, Gly, Thr and Ser, and Yyy is an amino acid selected from the group consisting of Val, Leu, Nle, Ile and Phe.

6. The analog or pharmaceutically acceptable salt thereof of claim 1, wherein the carboxy terminus modification is an amide or an alkylamide.

7. A pharmaceutical preparation comprising the analog or pharmaceutically acceptable salt thereof of claim 1, and a pharmaceutically-acceptable carrier.

8. A method for treating osteoporosis in a patient in need of such treatment comprising administering an effective amount of the analog or pharmaceutically acceptable salt thereof of claim 1, to the patient to treat the osteoporosis.

9. A method for promoting bone formation in a patient in need of such treatment comprising administering an effective amount of the analog or pharmaceutically acceptable salt thereof of claim 1, to the patient to promote bone formation.

10. A method for inhibiting bone loss in a patient in need of such treatment comprising administering an effective amount of the analog or pharmaceutically acceptable salt thereof of claim 1, to the patient to inhibit bone loss.

* * * * *

SEQUENCE LISTING

<160> NUMBER OF SEQ ID NOS: 43

<210> SEQ ID NO 1
<211> LENGTH: 34
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

-continued

Asn Phe

<210> SEQ ID NO 2
<211> LENGTH: 34
<212> TYPE: PRT
<213> ORGANISM: Bos taurus

<400> SEQUENCE: 2

Ala Val Ser Glu Ile Gln Phe Met His Asn Leu Gly Lys His Leu Ser
1               5                   10                  15

Ser Met Glu Arg Val Glu Trp Leu Arg Lys Lys Leu Gln Asp Val His
            20                  25                  30

Asn Phe

<210> SEQ ID NO 3
<211> LENGTH: 34
<212> TYPE: PRT
<213> ORGANISM: Homo sapiens

<400> SEQUENCE: 3

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala

<210> SEQ ID NO 4
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (1)..(2)
<223> OTHER INFORMATION: reduced peptide bond between the residues
<220> FEATURE:
<221> NAME/KEY: MISC_FEATURE
<222> LOCATION: (8)..(8)
<223> OTHER INFORMATION: Xaa = norleucine (Nle)
<220> FEATURE:
<221> NAME/KEY: MISC_FEATURE
<222> LOCATION: (12)..(12)
<223> OTHER INFORMATION: Xaa = 2-aminoisobutyric acid (Aib)
<220> FEATURE:
<221> NAME/KEY: MISC_FEATURE
<222> LOCATION: (18)..(18)
<223> OTHER INFORMATION: Xaa = norleucine (Nle)
<220> FEATURE:
<221> NAME/KEY: MISC_FEATURE
<222> LOCATION: (23)..(23)
<223> OTHER INFORMATION: Xaa = 2-napthyl-alanine (2-Nal)

<400> SEQUENCE: 4

Ala Val Ser Glu Ile Gln Phe Xaa His Asn Leu Xaa Lys His Leu Ser
1               5                   10                  15

Ser Xaa Glu Arg Val Glu Xaa Leu Arg Lys Lys Leu Gln Asp Val His
            20                  25                  30

Asn Tyr

<210> SEQ ID NO 5
<211> LENGTH: 34
<212> TYPE: PRT
<213> ORGANISM: Artificial
<220> FEATURE:
<223> OTHER INFORMATION: Designed sequence

<400> SEQUENCE: 5

Ser Val Ser Glu Ile Gln Leu Met His Asn Leu Gly Lys His Leu Asn
1               5                   10                  15

Ser Met Glu Arg Val Glu Leu Leu Glu Lys Leu Leu Glu Lys Leu His
            20                  25                  30

Asn Phe

<210> SEQ ID NO 6
<211> LENGTH: 34
<212> TYPE: PRT
<213> ORGANISM: Artificial
<220> FEATURE:
<223> OTHER INFORMATION: Designed sequence

<400> SEQUENCE: 6

Ser Val Ser Glu Ile Gln Leu Met His Asn Leu Gly Lys His Leu Asn
1               5                   10                  15

Ser Met Glu Arg Val Glu Trp Leu Ser Lys Lys Leu Glu Lys Val His
            20                  25                  30

Asn Phe

<210> SEQ ID NO 7
<211> LENGTH: 34
<212> TYPE: PRT
<213> ORGANISM: Artificial
<220> FEATURE:
<223> OTHER INFORMATION: Designed sequence

<400> SEQUENCE: 7

Ser Val Ser Glu Ile Gln Leu Met His Asn Leu Gly Lys His Leu Asn
1               5                   10                  15

Ser Met Glu Arg Val Glu Leu Leu Arg Lys Leu Leu Gln Asp Leu His
            20                  25                  30

Asn Phe

<210> SEQ ID NO 8
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (26)..(26)
<223> OTHER INFORMATION: Xaa = 2-aminoisobutyric acid (Aib)

<400> SEQUENCE: 8

Ala Val Ser Glu His Gln Leu Leu His Asp Lys Gly Lys Ser Ile Gln
1               5                   10                  15

Asp Leu Arg Arg Arg Phe Phe Leu His Xaa Leu Ile Ala Glu Ile His
            20                  25                  30

Thr Ala

<210> SEQ ID NO 9
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (32)..(32)

<223> OTHER INFORMATION: Xaa = 2-thienyl-alanine (Thi)

<400> SEQUENCE: 9

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Lys Leu Xaa
            20                  25                  30

Thr Ala

<210> SEQ ID NO 10
<211> LENGTH: 34
<212> TYPE: PRT
<213> ORGANISM: Artificial
<220> FEATURE:
<223> OTHER INFORMATION: Designed sequence

<400> SEQUENCE: 10

Ala Val Ser Glu His Gln Leu Leu His Asp Lys Gly Lys Ser Ile Gln
1               5                   10                  15

Asp Leu Arg Arg Arg Glu Leu Leu Glu Lys Leu Leu Glu Leu Leu His
            20                  25                  30

Thr Ala

<210> SEQ ID NO 11
<211> LENGTH: 34
<212> TYPE: PRT
<213> ORGANISM: Artificial
<220> FEATURE:
<223> OTHER INFORMATION: Designed sequence

<400> SEQUENCE: 11

Ala Val Ser Glu His Gln Leu Leu His Asp Lys Gly Lys Ser Ile Gln
1               5                   10                  15

Asp Leu Arg Arg Arg Phe Leu Leu His His Leu Leu Ala Glu Leu His
            20                  25                  30

Thr Ala

<210> SEQ ID NO 12
<211> LENGTH: 34
<212> TYPE: PRT
<213> ORGANISM: Artificial
<220> FEATURE:
<223> OTHER INFORMATION: Designed sequence

<400> SEQUENCE: 12

Ala Val Ser Glu His Gln Leu Leu His Asp Lys Gly Lys Ser Ile Gln
1               5                   10                  15

Asp Leu Arg Arg Arg Glu Phe Leu Glu Lys Leu Ile Glu Lys Ile His
            20                  25                  30

Thr Ala

<210> SEQ ID NO 13
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (8)..(8)
<223> OTHER INFORMATION: Xaa = norleucine (Nle)
<220> FEATURE:
<221> NAME/KEY: MISC_FEATURE

```
<222> LOCATION: (18)..(18)
<223> OTHER INFORMATION: Xaa = beta-alanine
<220> FEATURE:
<221> NAME/KEY: MISC_FEATURE
<222> LOCATION: (23)..(23)
<223> OTHER INFORMATION: Xaa = 2-napthyl-alanine (2-Nal)

<400> SEQUENCE: 13

Ala Val Ser Glu Ile Gln Phe Xaa His Asn Leu Gly Lys His Leu Ser
1               5                   10                  15

Ser Xaa Glu Arg Val Glu Xaa Leu Arg Lys Lys Leu Gln Asp Val His
            20                  25                  30

Asn Tyr

<210> SEQ ID NO 14
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (8)..(8)
<223> OTHER INFORMATION: Xaa = norleucine (Nle)
<220> FEATURE:
<221> NAME/KEY: MISC_FEATURE
<222> LOCATION: (18)..(18)
<223> OTHER INFORMATION: Xaa = beta-alanine
<220> FEATURE:
<221> NAME/KEY: MISC_FEATURE
<222> LOCATION: (19)..(19)
<223> OTHER INFORMATION: Xaa = beta-alanine
<220> FEATURE:
<221> NAME/KEY: MISC_FEATURE
<222> LOCATION: (23)..(23)
<223> OTHER INFORMATION: Xaa = 2-naphthyl-alanine (2-Nal)

<400> SEQUENCE: 14

Ala Val Ser Glu Ile Gln Phe Xaa His Asn Leu Gly Lys His Leu Ser
1               5                   10                  15

Ser Xaa Xaa Arg Val Glu Xaa Leu Arg Lys Lys Leu Gln Asp Val His
            20                  25                  30

Asn Tyr

<210> SEQ ID NO 15
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (8)..(8)
<223> OTHER INFORMATION: Xaa = norleucine (Nle)
<220> FEATURE:
<221> NAME/KEY: MISC_FEATURE
<222> LOCATION: (18)..(18)
<223> OTHER INFORMATION: Xaa = Norleucine (Nle)
<220> FEATURE:
<221> NAME/KEY: MISC_FEATURE
<222> LOCATION: (19)..(19)
<223> OTHER INFORMATION: Xaa = beta-alanine
<220> FEATURE:
<221> NAME/KEY: MISC_FEATURE
<222> LOCATION: (23)..(23)
<223> OTHER INFORMATION: Xaa = 2-naphthyl-alanine (2-Nal)

<400> SEQUENCE: 15

Ala Val Ser Glu Ile Gln Phe Xaa His Asn Leu Gly Lys His Leu Ser
1               5                   10                  15
```

```
Ser Xaa Xaa Arg Val Glu Xaa Leu Arg Lys Lys Leu Gln Asp Val His
        20              25                  30

Asn Tyr

<210> SEQ ID NO 16
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (8)..(8)
<223> OTHER INFORMATION: Xaa = Norleucine (Nle)
<220> FEATURE:
<221> NAME/KEY: MISC_FEATURE
<222> LOCATION: (18)..(18)
<223> OTHER INFORMATION: Xaa = beta-homo-leucine
<220> FEATURE:
<221> NAME/KEY: MISC_FEATURE
<222> LOCATION: (19)..(19)
<223> OTHER INFORMATION: Xaa = beta-alanine
<220> FEATURE:
<221> NAME/KEY: MISC_FEATURE
<222> LOCATION: (23)..(23)
<223> OTHER INFORMATION: Xaa = 2-naphthyl-alanine (2-Nal)

<400> SEQUENCE: 16

Ala Val Ser Glu Ile Gln Phe Xaa His Asn Leu Gly Lys His Leu Ser
1               5                   10                  15

Ser Xaa Xaa Arg Val Glu Xaa Leu Arg Lys Lys Leu Gln Asp Val His
        20              25                  30

Asn Tyr

<210> SEQ ID NO 17
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (8)..(8)
<223> OTHER INFORMATION: Xaa = norleucine (Nle)
<220> FEATURE:
<221> NAME/KEY: MISC_FEATURE
<222> LOCATION: (17)..(17)
<223> OTHER INFORMATION: Xaa = beta-alanine
<220> FEATURE:
<221> NAME/KEY: MISC_FEATURE
<222> LOCATION: (18)..(18)
<223> OTHER INFORMATION: Xaa = beta-homo-leucine
<220> FEATURE:
<221> NAME/KEY: MISC_FEATURE
<222> LOCATION: (19)..(19)
<223> OTHER INFORMATION: Xaa = beta-alanine
<220> FEATURE:
<221> NAME/KEY: MISC_FEATURE
<222> LOCATION: (23)..(23)
<223> OTHER INFORMATION: Xaa = 2-naphthyl-alanine (2-Nal)

<400> SEQUENCE: 17

Ala Val Ser Glu Ile Gln Phe Xaa His Asn Leu Gly Lys His Leu Ser
1               5                   10                  15

Xaa Xaa Xaa Arg Val Glu Xaa Leu Arg Lys Lys Leu Gln Asp Val His
        20              25                  30

Asn Tyr
```

```
<210> SEQ ID NO 18
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (16)..(16)
<223> OTHER INFORMATION: Xaa = beta-alanine
<220> FEATURE:
<221> NAME/KEY: MISC_FEATURE
<222> LOCATION: (18)..(18)
<223> OTHER INFORMATION: Xaa = norleucine (Nle)

<400> SEQUENCE: 18

Ala Val Ser Glu Ile Gln Phe Met His Asn Leu Gly Lys His Leu Xaa
1               5                   10                  15

Ser Xaa Glu Arg Val Glu Trp Leu Arg Lys Lys Leu Gln Asp Val His
            20                  25                  30

Asn Phe

<210> SEQ ID NO 19
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (18)..(18)
<223> OTHER INFORMATION: Xaa = norleucine (Nle)
<220> FEATURE:
<221> NAME/KEY: MISC_FEATURE
<222> LOCATION: (20)..(20)
<223> OTHER INFORMATION: Xaa = beta-alanine

<400> SEQUENCE: 19

Ala Val Ser Glu Ile Gln Phe Met His Asn Leu Gly Lys His Leu Ser
1               5                   10                  15

Ser Xaa Glu Xaa Val Glu Trp Leu Arg Lys Lys Leu Gln Asp Val His
            20                  25                  30

Asn Phe

<210> SEQ ID NO 20
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (17)..(17)
<223> OTHER INFORMATION: Xaa = beta-alanine
<220> FEATURE:
<221> NAME/KEY: MISC_FEATURE
<222> LOCATION: (18)..(18)
<223> OTHER INFORMATION: Xaa = norleucine (Nle)

<400> SEQUENCE: 20

Ala Val Ser Glu Ile Gln Phe Met His Asn Leu Gly Lys His Leu Ser
1               5                   10                  15

Xaa Xaa Glu Arg Val Glu Trp Leu Arg Lys Lys Leu Gln Asp Val His
            20                  25                  30

Asn Phe

<210> SEQ ID NO 21
```

```
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (18)..(18)
<223> OTHER INFORMATION: Xaa = beta-alanine

<400> SEQUENCE: 21
```

Ala Val Ser Glu Ile Gln Phe Met His Asn Leu Gly Lys His Leu Ser
1               5                   10                  15

Ser Xaa Glu Arg Val Glu Trp Leu Arg Lys Lys Leu Gln Asp Val His
            20                  25                  30

Asn Phe

```
<210> SEQ ID NO 22
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (18)..(18)
<223> OTHER INFORMATION: Xaa = norleucine (Nle)
<220> FEATURE:
<221> NAME/KEY: MISC_FEATURE
<222> LOCATION: (19)..(19)
<223> OTHER INFORMATION: Xaa = beta-alanine

<400> SEQUENCE: 22
```

Ala Val Ser Glu Ile Gln Phe Met His Asn Leu Gly Lys His Leu Ser
1               5                   10                  15

Ser Xaa Xaa Arg Val Glu Trp Leu Arg Lys Lys Leu Gln Asp Val His
            20                  25                  30

Asn Phe

```
<210> SEQ ID NO 23
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (17)..(17)
<223> OTHER INFORMATION: Xaa = beta-homo-serine
<220> FEATURE:
<221> NAME/KEY: MISC_FEATURE
<222> LOCATION: (18)..(18)
<223> OTHER INFORMATION: Xaa = norleucine (Nle)

<400> SEQUENCE: 23
```

Ala Val Ser Glu Ile Gln Phe Met His Asn Leu Gly Lys His Leu Ser
1               5                   10                  15

Xaa Xaa Glu Arg Val Glu Trp Leu Arg Lys Lys Leu Gln Asp Val His
            20                  25                  30

Asn Phe

```
<210> SEQ ID NO 24
<211> LENGTH: 34
<212> TYPE: PRT
<213> ORGANISM: Artificial
<220> FEATURE:
<223> OTHER INFORMATION: Designed sequence
```

```
<220> FEATURE:
<221> NAME/KEY: MISC_FEATURE
<222> LOCATION: (18)..(18)
<223> OTHER INFORMATION: Xaa = beta-homo-leucine

<400> SEQUENCE: 24

Ala Val Ser Glu Ile Gln Phe Met His Asn Leu Gly Lys His Leu Ser
1               5                   10                  15

Ser Xaa Glu Arg Val Glu Trp Leu Arg Lys Lys Leu Gln Asp Val His
            20                  25                  30

Asn Phe

<210> SEQ ID NO 25
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (18)..(18)
<223> OTHER INFORMATION: Xaa = norleucine (Nle)
<220> FEATURE:
<221> NAME/KEY: MISC_FEATURE
<222> LOCATION: (19)..(19)
<223> OTHER INFORMATION: Xaa = beta-homo-glutamic acid

<400> SEQUENCE: 25

Ala Val Ser Glu Ile Gln Phe Met His Asn Leu Gly Lys His Leu Ser
1               5                   10                  15

Ser Xaa Xaa Arg Val Glu Trp Leu Arg Lys Lys Leu Gln Asp Val His
            20                  25                  30

Asn Phe

<210> SEQ ID NO 26
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (17)..(17)
<223> OTHER INFORMATION: Xaa = beta-alanine
<220> FEATURE:
<221> NAME/KEY: MISC_FEATURE
<222> LOCATION: (18)..(18)
<223> OTHER INFORMATION: Xaa = beta-alanine

<400> SEQUENCE: 26

Ala Val Ser Glu Ile Gln Phe Met His Asn Leu Gly Lys His Leu Ser
1               5                   10                  15

Xaa Xaa Glu Arg Val Glu Trp Leu Arg Lys Lys Leu Gln Asp Val His
            20                  25                  30

Asn Phe

<210> SEQ ID NO 27
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (18)..(18)
<223> OTHER INFORMATION: Xaa = beta-alanine
<220> FEATURE:
```

```
<221> NAME/KEY: MISC_FEATURE
<222> LOCATION: (19)..(19)
<223> OTHER INFORMATION: Xaa = beta-alanine

<400> SEQUENCE: 27

Ala Val Ser Glu Ile Gln Phe Met His Asn Leu Gly Lys His Leu Ser
1               5                   10                  15

Ser Xaa Xaa Arg Val Glu Trp Leu Arg Lys Lys Leu Gln Asp Val His
            20                  25                  30

Asn Phe

<210> SEQ ID NO 28
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (17)..(17)
<223> OTHER INFORMATION: Xaa = beta-alanine
<220> FEATURE:
<221> NAME/KEY: MISC_FEATURE
<222> LOCATION: (18)..(18)
<223> OTHER INFORMATION: Xaa = norleucine (Nle)
<220> FEATURE:
<221> NAME/KEY: MISC_FEATURE
<222> LOCATION: (19)..(19)
<223> OTHER INFORMATION: Xaa = beta-alanine

<400> SEQUENCE: 28

Ala Val Ser Glu Ile Gln Phe Met His Asn Leu Gly Lys His Leu Ser
1               5                   10                  15

Xaa Xaa Xaa Arg Val Glu Trp Leu Arg Lys Lys Leu Gln Asp Val His
            20                  25                  30

Asn Phe

<210> SEQ ID NO 29
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (17)..(17)
<223> OTHER INFORMATION: Xaa = beta-alanine
<220> FEATURE:
<221> NAME/KEY: MISC_FEATURE
<222> LOCATION: (18)..(18)
<223> OTHER INFORMATION: Xaa = beta-homo-leucine

<400> SEQUENCE: 29

Ala Val Ser Glu Ile Gln Phe Met His Asn Leu Gly Lys His Leu Ser
1               5                   10                  15

Xaa Xaa Glu Arg Val Glu Trp Leu Arg Lys Lys Leu Gln Asp Val His
            20                  25                  30

Asn Phe

<210> SEQ ID NO 30
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
```

```
<222> LOCATION: (18)..(18)
<223> OTHER INFORMATION: Xaa = beta-homo-leucine
<220> FEATURE:
<221> NAME/KEY: MISC_FEATURE
<222> LOCATION: (19)..(19)
<223> OTHER INFORMATION: Xaa = beta-alanine

<400> SEQUENCE: 30

Ala Val Ser Glu Ile Gln Phe Met His Asn Leu Gly Lys His Leu Ser
1               5                   10                  15

Ser Xaa Xaa Arg Val Glu Trp Leu Arg Lys Lys Leu Gln Asp Val His
            20                  25                  30

Asn Phe

<210> SEQ ID NO 31
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (18)..(18)
<223> OTHER INFORMATION: Xaa = beta-alanine
<220> FEATURE:
<221> NAME/KEY: MISC_FEATURE
<222> LOCATION: (19)..(19)
<223> OTHER INFORMATION: Xaa = beta-homo-glutamic acid

<400> SEQUENCE: 31

Ala Val Ser Glu Ile Gln Phe Met His Asn Leu Gly Lys His Leu Ser
1               5                   10                  15

Ser Xaa Xaa Arg Val Glu Trp Leu Arg Lys Lys Leu Gln Asp Val His
            20                  25                  30

Asn Phe

<210> SEQ ID NO 32
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (17)..(17)
<223> OTHER INFORMATION: Xaa = beta-alanine
<220> FEATURE:
<221> NAME/KEY: MISC_FEATURE
<222> LOCATION: (18)..(18)
<223> OTHER INFORMATION: Xaa = norleucine (Nle)
<220> FEATURE:
<221> NAME/KEY: MISC_FEATURE
<222> LOCATION: (19)..(19)
<223> OTHER INFORMATION: Xaa = beta-homo-glutamic acid

<400> SEQUENCE: 32

Ala Val Ser Glu Ile Gln Phe Met His Asn Leu Gly Lys His Leu Ser
1               5                   10                  15

Xaa Xaa Xaa Arg Val Glu Trp Leu Arg Lys Lys Leu Gln Asp Val His
            20                  25                  30

Asn Phe

<210> SEQ ID NO 33
<211> LENGTH: 34
<212> TYPE: PRT
<213> ORGANISM: Artificial
<220> FEATURE:
```

```
<223> OTHER INFORMATION: Designed sequence
<220> FEATURE:
<221> NAME/KEY: MISC_FEATURE
<222> LOCATION: (17)..(17)
<223> OTHER INFORMATION: Xaa = beta-homo-serine
<220> FEATURE:
<221> NAME/KEY: MISC_FEATURE
<222> LOCATION: (18)..(18)
<223> OTHER INFORMATION: Xaa = norleucine (Nle)
<220> FEATURE:
<221> NAME/KEY: MISC_FEATURE
<222> LOCATION: (19)..(19)
<223> OTHER INFORMATION: Xaa = beta-alanine

<400> SEQUENCE: 33

Ala Val Ser Glu Ile Gln Phe Met His Asn Leu Gly Lys His Leu Ser
1               5                   10                  15

Xaa Xaa Xaa Arg Val Glu Trp Leu Arg Lys Lys Leu Gln Asp Val His
            20                  25                  30

Asn Phe

<210> SEQ ID NO 34
<211> LENGTH: 35
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (17)..(17)
<223> OTHER INFORMATION: Xaa = beta-homo-serine
<220> FEATURE:
<221> NAME/KEY: MISC_FEATURE
<222> LOCATION: (18)..(18)
<223> OTHER INFORMATION: Xaa = norleucine (Nle)
<220> FEATURE:
<221> NAME/KEY: MISC_FEATURE
<222> LOCATION: (19)..(19)
<223> OTHER INFORMATION: Xaa = beta-alanine

<400> SEQUENCE: 34

Ala Val Ser Glu Ile Gln Phe Met His Asn Leu Gly Lys His Leu Ser
1               5                   10                  15

Xaa Xaa Xaa Glu Arg Val Glu Trp Leu Arg Lys Lys Leu Gln Asp Val
            20                  25                  30

His Asn Phe
        35

<210> SEQ ID NO 35
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (17)..(17)
<223> OTHER INFORMATION: Xaa = beta-homo-serine
<220> FEATURE:
<221> NAME/KEY: MISC_FEATURE
<222> LOCATION: (18)..(18)
<223> OTHER INFORMATION: Xaa = beta-alanine
<220> FEATURE:
<221> NAME/KEY: MISC_FEATURE
<222> LOCATION: (19)..(19)
<223> OTHER INFORMATION: Xaa = beta-alanine

<400> SEQUENCE: 35

Ala Val Ser Glu Ile Gln Phe Met His Asn Leu Gly Lys His Leu Ser
1               5                   10                  15
```

```
Xaa Xaa Xaa Arg Val Glu Trp Leu Arg Lys Lys Leu Gln Asp Val His
        20                  25                  30

Asn Phe

<210> SEQ ID NO 36
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (17)..(17)
<223> OTHER INFORMATION: Xaa = beta-alanine
<220> FEATURE:
<221> NAME/KEY: MISC_FEATURE
<222> LOCATION: (18)..(18)
<223> OTHER INFORMATION: Xaa = beta-alanine
<220> FEATURE:
<221> NAME/KEY: MISC_FEATURE
<222> LOCATION: (19)..(19)
<223> OTHER INFORMATION: Xaa = beta-homo-glutamic acid

<400> SEQUENCE: 36

Ala Val Ser Glu Ile Gln Phe Met His Asn Leu Gly Lys His Leu Ser
1               5                   10                  15

Xaa Xaa Xaa Arg Val Glu Trp Leu Arg Lys Lys Leu Gln Asp Val His
        20                  25                  30

Asn Phe

<210> SEQ ID NO 37
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (17)..(17)
<223> OTHER INFORMATION: Xaa = beta-alanine
<220> FEATURE:
<221> NAME/KEY: MISC_FEATURE
<222> LOCATION: (18)..(18)
<223> OTHER INFORMATION: Xaa = beta-homo-leucine
<220> FEATURE:
<221> NAME/KEY: MISC_FEATURE
<222> LOCATION: (19)..(19)
<223> OTHER INFORMATION: Xaa = beta-alanine

<400> SEQUENCE: 37

Ala Val Ser Glu Ile Gln Phe Met His Asn Leu Gly Lys His Leu Ser
1               5                   10                  15

Xaa Xaa Xaa Arg Val Glu Trp Leu Arg Lys Lys Leu Gln Asp Val His
        20                  25                  30

Asn Phe

<210> SEQ ID NO 38
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (17)..(17)
<223> OTHER INFORMATION: Xaa = beta-homo-serine
<220> FEATURE:
<221> NAME/KEY: MISC_FEATURE
```

```
<222> LOCATION: (18)..(18)
<223> OTHER INFORMATION: Xaa = beta-homo-leucine

<400> SEQUENCE: 38

Ala Val Ser Glu Ile Gln Phe Met His Asn Leu Gly Lys His Leu Ser
1               5                   10                  15

Xaa Xaa Glu Arg Val Glu Trp Leu Arg Lys Lys Leu Gln Asp Val His
            20                  25                  30

Asn Phe

<210> SEQ ID NO 39
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (18)..(18)
<223> OTHER INFORMATION: Xaa = beta-homo-leucine
<220> FEATURE:
<221> NAME/KEY: MISC_FEATURE
<222> LOCATION: (19)..(19)
<223> OTHER INFORMATION: Xaa = beta-homo-glutamic acid

<400> SEQUENCE: 39

Ala Val Ser Glu Ile Gln Phe Met His Asn Leu Gly Lys His Leu Ser
1               5                   10                  15

Ser Xaa Xaa Arg Val Glu Trp Leu Arg Lys Lys Leu Gln Asp Val His
            20                  25                  30

Asn Phe

<210> SEQ ID NO 40
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (17)..(17)
<223> OTHER INFORMATION: Xaa = beta-homo-serine
<220> FEATURE:
<221> NAME/KEY: MISC_FEATURE
<222> LOCATION: (18)..(18)
<223> OTHER INFORMATION: Xaa = norleucine (Nle)
<220> FEATURE:
<221> NAME/KEY: MISC_FEATURE
<222> LOCATION: (19)..(19)
<223> OTHER INFORMATION: Xaa = betao-homo-glutamic acid

<400> SEQUENCE: 40

Ala Val Ser Glu Ile Gln Phe Met His Asn Leu Gly Lys His Leu Ser
1               5                   10                  15

Xaa Xaa Xaa Arg Val Glu Trp Leu Arg Lys Lys Leu Gln Asp Val His
            20                  25                  30

Asn Phe

<210> SEQ ID NO 41
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (17)..(17)
```

```
<223> OTHER INFORMATION: Xaa = beta-homo-serine
<220> FEATURE:
<221> NAME/KEY: MISC_FEATURE
<222> LOCATION: (18)..(18)
<223> OTHER INFORMATION: Xaa = beta-homo-leucine
<220> FEATURE:
<221> NAME/KEY: MISC_FEATURE
<222> LOCATION: (19)..(19)
<223> OTHER INFORMATION: Xaa = beta-homo-glutamic acid

<400> SEQUENCE: 41

Ala Val Ser Glu Ile Gln Phe Met His Asn Leu Gly Lys His Leu Ser
1               5                   10                  15

Xaa Xaa Xaa Arg Val Glu Trp Leu Arg Lys Lys Leu Gln Asp Val His
            20                  25                  30

Asn Phe

<210> SEQ ID NO 42
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (1)..(2)
<223> OTHER INFORMATION: reduced peptide bond between the residues
<220> FEATURE:
<221> NAME/KEY: MISC_FEATURE
<222> LOCATION: (8)..(8)
<223> OTHER INFORMATION: Xaa = norleucine (Nle)
<220> FEATURE:
<221> NAME/KEY: MISC_FEATURE
<222> LOCATION: (12)..(12)
<223> OTHER INFORMATION: Xaa = 2-aminoisobutyric acid (Aib)
<220> FEATURE:
<221> NAME/KEY: MISC_FEATURE
<222> LOCATION: (18)..(18)
<223> OTHER INFORMATION: Xaa = norleucine (Nle)
<220> FEATURE:
<221> NAME/KEY: MISC_FEATURE
<222> LOCATION: (23)..(23)
<223> OTHER INFORMATION: Xaa = 2-naphthyl-alanine (2-Nal)
<220> FEATURE:
<221> NAME/KEY: MISC_FEATURE
<222> LOCATION: (34)..(34)
<223> OTHER INFORMATION: Xaa = 2-naphthyl-alanine (2-Nal)

<400> SEQUENCE: 42

Ser Val Ser Glu Ile Gln Leu Xaa His Asn Leu Xaa Lys His Leu Asn
1               5                   10                  15

Ser Xaa Glu Arg Val Glu Xaa Leu Arg Lys Lys Leu Gln Asp Val His
            20                  25                  30

Asn Tyr

<210> SEQ ID NO 43
<211> LENGTH: 34
<212> TYPE: PRT
<213> ORGANISM: Artificial
<220> FEATURE:
<223> OTHER INFORMATION: Designed sequence
<220> FEATURE:
<221> NAME/KEY: MISC_FEATURE
<222> LOCATION: (1)..(2)
<223> OTHER INFORMATION: reduced peptide bond between the residues
<220> FEATURE:
<221> NAME/KEY: MISC_FEATURE
<222> LOCATION: (12)..(12)
<223> OTHER INFORMATION: Xaa = 2-aminoisobutyric acid (Aib)

<400> SEQUENCE: 43
```

```
Ser Val Ser Glu His Gln Leu Leu His Asp Lys Xaa Lys Ser Ile Gln
1               5                   10                  15

Asp Leu Arg Arg Arg Phe Phe Leu His His Leu Ile Ala Glu Ile His
                20                  25                  30

Thr Ala
```